United States Patent [19]

Jones

[11] Patent Number: 5,711,900
[45] Date of Patent: Jan. 27, 1998

[54] GADOLINIUM COMPOUNDS FOR USE AS OIL-SOLUBLE TRACERS

[75] Inventor: Timothy G. J. Jones, Bethel, Conn.

[73] Assignee: Schlumberger Technology Corporation, Ridgefield, Conn.

[21] Appl. No.: 564,000

[22] Filed: Nov. 29, 1995

[51] Int. Cl.⁶ .............................. G01N 31/00; C09K 7/00
[52] U.S. Cl. ................ 252/408.1; 252/517; 252/518; 252/521; 252/600; 252/645; 250/260; 250/965; 567/905
[58] Field of Search .................. 252/408.1, 600, 252/645, 517, 521, 518; 250/260, 965; 507/905

[56] References Cited

U.S. PATENT DOCUMENTS

| | | | |
|---|---|---|---|
| 3,784,828 | 1/1974 | Hayes | 250/106 L |
| 3,970,561 | 7/1976 | Sievers et al. | 210/198 C |
| 4,166,215 | 8/1979 | Anderson | 250/260 |
| 4,166,216 | 8/1979 | Cubberly, Jr. | 250/260 |
| 4,233,508 | 11/1980 | Arnold | 250/259 |
| 4,423,152 | 12/1983 | Lewis et al. | 436/56 |
| 4,522,631 | 6/1985 | Mourao et al. | 44/57 |
| 4,755,469 | 7/1988 | Showalter et al. | 436/27 |
| 4,825,072 | 4/1989 | McWhirter et al. | 250/259 |
| 4,962,264 | 10/1990 | Forester | 585/648 |
| 5,047,632 | 9/1991 | Hunt | 250/302 |
| 5,108,636 | 4/1992 | Leising et al. | 252/62.54 |
| 5,306,911 | 4/1994 | Hunt | 250/302 |
| 5,407,560 | 4/1995 | Miyawaki et al. | 208/106 |
| 5,543,617 | 8/1996 | Roscoe et al. | 250/259 |

*Primary Examiner*—Sharon Gibson
*Assistant Examiner*—Deanna Baxam
*Attorney, Agent, or Firm*—Keith G. W. Smith

[57] ABSTRACT

A tracer solution suitable for use in measuring flow velocities in a borehole, includes: a) a gadolinium salt of a carboxylic acid of general formula $$R-\underset{\underset{R_2}{|}}{\overset{\overset{R_1}{|}}{C}}-CO_2H$$

where R is an alkyl of not less than four carbon atoms, typically C4 or C5 alkyl, and $R_1$ and $R_2$ are hydrogen or an alkyl group, typically hydrogen, methyl or ethyl; b) a free branched-chain carboxylic acid such as an excess of the acid used to form the Gd salt; and c) a non-polar solvent such as hexane or heptane. The Gd content of the solution should be not less than about 50 g/l and is best when it is as high as possible, for example greater than 100 g/l, and the viscosity should be less than 20 cP.

14 Claims, No Drawings

GADOLINIUM COMPOUNDS FOR USE AS OIL-SOLUBLE TRACERS

FIELD OF THE INVENTION

The present invention relates gadolinium-containing compounds for use in oil-soluble tracer solutions, and to tracers comprising such solutions. In particular the invention provides tracer compounds for use in a method of measuring the flow velocity of a hydrocarbon phase in a multiphase flow and finds application in measuring flow velocities in hydrocarbon-producing wells.

BACKGROUND OF THE INVENTION

The fluids produced by a hydrocarbon well typically comprise a hydrocarbon (oil) phase and an aqueous (water) phase and sometimes a gas phase. One of these phases, often the aqueous phase, is continuous and the other phase is dispersed therein. Knowledge of the proportions of these phases and their flow velocities is required to determine the flow rates from the well of the various phases. Many methods have been proposed for determining flow velocities in single-phase or multi-phase flows. One particular approach which is applicable to measuring flows in wells is to introduce tracers into the flow and to measure the passage of these tracers past a measurement station to make a measurement of the flow. One example of a tracer technique is the introduction of a saline solution into the flow and the measurement of the change in electrical conductivity as the tracer passes the measurement station. However, problems can arise due to the natural salinity of the formation water and such a technique only measures the aqueous phase and so cannot be used in isolation to provide all of the required measurements in a hydrocarbon well. As an alternative to saline solutions, radioactive tracers have been used to measure single-phase and multi-phase flows. These tracers can be made either oil-soluble or water-soluble and so the technique can be used to measure both phases in a hydrocarbon well. One example of the use of radioactive tracers to determine water flow behind casing (outside the well) is found in U.S. Pat. No. 3,784,828. An example of a tool used to make such measurements of flow inside hydrocarbon wells is the Tracer Ejection Tool of Schlumberger which is described in U.S. Pat. No. 4,166,215 and U.S. Pat. No. 4,166,216. Minor amounts of suitable radioactive tracer such as iodine 131 are periodically discharged into the continuous-phase well fluid at a selected depth location in the well. Thereafter, by simultaneously measuring the level of radioactivity above and below that location, measurements are obtained which are representative of one or more dynamic flow characteristics of the continuous phase. These measurements are based on the travel time of the tracer from the location where it is discharged into the flow to the measurement stations. Since the ejection of radioactive materials into the fluids that are subsequently produced from the well is often considered undesirable, alternative methods using nuclear radiation techniques have been proposed. These alternative techniques produce short-lived activation components in the flow to provide the radioactive material which is detected, but which is no longer radioactive by the time the fluids are produced from the well. An example of this is found in U.S. Pat. No. 4,233,508 in which the fluid being monitored is irradiated with neutrons such that oxygen atoms are transformed into radioactive nitrogen atoms which decay by emitting $\gamma$ radiation which is detected at the measurement station. This method of activating a component of the flow only measures the aqueous phase since the oil phase does not include a significant concentration of oxygen atoms which become activated by neutron radiation. Further examples of the use of tracer ejection or activation techniques for measuring flows in wells are disclosed in U.S. Pat. No. 5,047,632 and U.S. Pat. No. 5,306,911.

U.S. Pat. No. 5,543,617 (incorporated herein by reference) discloses a method of measuring the flow velocity of one phase in a multi-phase flow, comprising the steps of creating a nuclear radiation environment around a measurement location in the flowing fluid at which radiation is detected; ejecting a tracer into the flowing fluid upstream of the measurement station which affects detection of the radiation at the measurement location as it passes; making a time-based measurement of the radiation at the measurement location to include passage of the tracer so as to determine the effect of the tracer on the detection of radiation; and using the time-based measurement to determine the flow velocity. A suitable tracer suggested for such a method is a gadolinium-containing compound. Suitable oil miscible tracers include gadolinium brine-in-oil emulsions and Gd tagged organic compounds which can also be oil-soluble. Brine-in-oil emulsions can be prepared using mineral oil, $GdCl_3$ brines, and a surfactant such as EMUL-HT. A suitable oil-soluble tracer has the general formula $Gd(RCOO)_3$ wherein R is typically $CH_3(CH_2)_4$. An alternative version of the tracer includes six additional $CH_2$ groups. The general preparation scheme is as follows: $Gd(X)_3 + RCOOH \rightarrow Gd(RCOO)_3 + H_2O + HX$, X being chloride or acetate.

To be effective as a tracer in such a technique, it is necessary that the tracer include a relatively high concentration of gadolinium. It is known that high concentrations of transition metals such as lead, cobalt and maganese can be dissolved in non-polar organic solvents using naphthenic and related acids. The resulting compounds have been used in a variety of applications, including drying agents in paint, insecticides/biocides and anti-knock additives in gasoline. A common feature of transition metal carboxylates is that their viscosities can be very high, even when dissolved in hydrocarbons at low concentrations; some heavy metal carboxylates have been used as lubricating greases. High viscosity is highly undesirable for a tracer for use in a technique such as that described in U.S. Pat. No. 5,543,617 since it prevents injection of controlled quantities into the flow and dispersion of the tracer throughout the oil phase prior to measurement.

Oil-soluble lanthanide compounds have been proposed for various uses. U.S. Pat. No. 4,755,469 discloses the use, as an oil-soluble tracer, of a Group VIB, Group VIIB or lanthanum series rare earth salt of a fatty acid having 5–35 carbon atoms. It is proposed to add the tracer to an oil to be traced and oil samples taken at a remote location and analyzed to see if the tracer, and hence the original oil, is present at that location. The analysis techniques proposed are typical laboratory analyses and the metal in the tracer is chosen so as to be readily distinguished from common formation fluid components. U.S. Pat. No. 4,522,631 discloses a diesel fuel soluble compound of a rare earth metal (including Gd) for use as a fuel performance modifier. The compound typically has 3–25 carbon atoms and metal carbonyls are preferred. These compounds, together with an oxygenated compound such as an alkylcarbitol, aldehyde, ketone, alcohol or ether, are added to the fuel to provide a solution of 0.001–0.1 wt% rare earth in fuel.

None of the prior Gd compounds have been found suitable for use in a tracer flow velocity measurement technique.

It is an object of the present invention to provide a Gd compound in a form which is oil-soluble and has sufficient Gd content to be useful as a tracer in flow velocity measurement technique.

SUMMARY OF THE INVENTION

In accordance with a broad aspect of the invention, there is provided a low-viscosity, oil-miscible, gadolinium solution, such as a tracer solution suitable for use in measuring flow velocities in a borehole, comprising: a) a gadolinium salt of a carboxylic acid of general formula

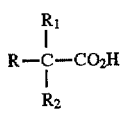

where R is an alkyl of not less than four carbon atoms, and $R_1$ and $R_2$ are selected from the group consisting of hydrogen and an alkyl group; b) a free branched-chain carboxylic acid; and c) an oil-miscible solvent, especially an organic, non-polar solvent.

The carboxylic acid forming the Gd salt preferably has R selected from C4 and C5 alkyl and $R_1$ and $R_2$ are selected from hydrogen, methyl and ethyl. When $R_1$ is hydrogen, $R_2$ is preferably methyl or ethyl. The Gd content of the solution should be not less than about 50 g/l and is best when it is as high as possible, for example greater than 100 g/l.

The free branched-chain carboxylic acid is typically the same as the acid used to form the Gd salt. When the acid forming the salt is not branched itself, i.e. $R_1$ and $R_2$ are hydrogen, a different acid must be present such as 3,5,5-trimethylhexanoic acid or 2-ethylhexanoic acid.

The non-polar solvent is typically a hydrocarbon having a density lower than that of water. Examples of suitable organic, non-polar solvents are hydrocarbons such as hexane and heptane. Suitable polar solvents might be long chain, branched alcohols, ethers or halogenated hydrocarbons.

It is particularly preferred that the solution has a viscosity of less than about 20 cP and a viscosity stabilizer such as tributyl citrate, oleyl alcohol, n-cyclohexyl-p-toluenesulphonamide and di(ethylene glycol) butyl ether can be included in the solution to maintain this level.

The present invention is particularly preferred for use in the measurement of velocity of oil phases in the multiphase flows common in oil wells, and involves a technique which specifically chooses the capture cross section of thermal neutrons produced by moderation in the formation and the borehole of 14 MeV neutrons produced by a DT neutron generator as the tracer physical property which is probed. This technique is described in U.S. Pat. No. 5,543,617 (incorporated herein by reference). The detector used is preferably a scintillation detector which responds to capture γ rays. Other neutron generators and detectors are possible, e.g. spectroscopic γ ray detectors or γ count rate detectors; the above choices are convenient because they already exist in forms which can be placed in a borehole. As mentioned, the tracer has a capture cross section which is different from that of the flowing material, which can be a combination of water, oil and gas. Typical components of borehole oil, water and gas have capture cross sections of less than 10 barns, with the exception of chlorine, which has a capture cross section of 33 barns. Gd, which has a capture cross section of 49000 barns, in its isotopically natural form is therefore highly preferred for this method.

DESCRIPTION OF THE PREFERRED EMBODIMENT

The tracer solution according to the present invention finds particular application as a non-radioactive tracer for use in a method of measuring the flow velocity of an oil phase in the flow from a hydrocarbon well, particularly a horizontal well. In order to be useful in such a method, the solution should have as high a Gd content as possible in order to improve the detection of the tracer in the well. Since it is necessary to place the tracer in an oil phase and there is usually a water phase present, it is also desirable that the solution should have a density which is less than that of water and should be miscible or soluble readily in oil and have a relatively low viscosity.

The basic composition of a solution according to the invention comprises: a) a gadolinium salt of a carboxylic acid of general formula

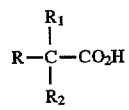

where R is an alkyl of not less than four carbon atoms, and $R_1$ and $R_2$ are selected from the group consisting of hydrogen and an alkyl group; b) a free branched-chain carboxylic acid; and c) a non-polar solvent.

The carboxylic acid forming the Gd salt preferably has R selected from C4 and C5 alkyl and $R_1$ and $R_2$ are selected from hydrogen, methyl and ethyl. Examples of suitable acids are hexanoic acid, 2-ethylhexanoic acid, neodecanoic acid, 2-methylhexanoic acid and 2,2-dimethylhexanoic acid.

The free branched-chain carboxylic acid is typically the same as the acid used to form the Gd salt. This can be achieved by use of an excess acid when producing the Gd salt as will be described below. The presence of free acid can also be found when an apparently stoichiometric quantity of acid is used in the production of the salt. When the acid forming the salt is not branched itself, such as hexanoic acid, a different acid must be present such as 3,5,5-trimethylhexanoic acid or 2-ethylhexanoic acid.

Examples of solutions according to the invention which have desired properties are summarized in Table 1 below:

TABLE 1

| Gd complex (Salt) | solvent | density (g/ml) | capillary viscosity[1] (cP) | Gd concentration (g/l) |
|---|---|---|---|---|
| 2-ethylhexanoate | heptane | 0.875 | 7.9 | 100.6 |
| 2-ethylhexanoate | hexane | 0.845 | 6.9 | 97.2 |
| 2-ethylhexanoate | heptane | 0.977 | 16.7 | 150.0 |
| 2-ethylhexanoate[2] | heptane | 0.837 | 19.8 | 100.0 |
| neodecanoate | heptane | 0.894 | 2.2 | 77.9 |
| 2-methylhexanoate | heptane | 0.840 | 2.2 | 100.0 |

[1]capillary viscosity measured at ambient temperature
[2]no excess acid added

It is particularly preferred that the solution should maintain a viscosity of less than about 20 cP in use. Since temperature cycling and aging have been found to have a detrimental effect of some Gd complexes, a viscosity stabilizer such as tributyl titrate, oleyl alcohol, n-cyclohexyl-p-toluenesulphonamide and di(ethylene glycol) butyl ether can be used. Tributyl citrate in an amount of about 3% has been found to maintain viscosity in solutions according to the invention.

The synthesis of the gadolinium carboxylate tracers is, in principle, straightforward with a direct reaction between the carboxylic acid ($RCO_2H$) and hydrated gadolinium hydroxide ($Gd(OH)_3 \cdot xH_2O$):

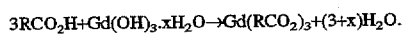

$$3RCO_2H + Gd(OH)_3 \cdot xH_2O \rightarrow Gd(RCO_2)_3 + (3+x)H_2O.$$

Gadolinium hydroxide is prepared by a precipitation reaction in water between a soluble gadolinium salt ($GdCl_3$, $Gd(NO_3)_3$, etc.) and a strong base:

$$GdX_3 + 3MOH \rightarrow Gd(OH)_3 + 3MX.$$

The gadolinium hydroxide used in the reaction with carboxylic acids is rapidly precipitated, filtered and copiously washed with water followed by dry acetone. Washing the gadolinium hydroxide precipitate with acetone immediately after precipitation appears to suppress its crystallization and results in the amorphous hydroxide required to produce the complexes used in the present invention.

The amorphous gadolinium hydroxide is reacted with the carboxylic acids at 85° C. (±5° C.) under constant mixing. The hydroxide is normally reacted with at least a 20% molar excess of a carboxylic acid. Examples of complexes have been produced using little or no excess acid, free acid is still found in the resulting complex. The high viscosity of the gadolinium carboxylate products prevents the reaction mixture from being stirred to completion.

Hydrated gadolinium carbonate ($Gd_2(CO_3)_3 \cdot xH_2O$) can be used in place of gadolinium hydroxide. However, since the carbonate has a lower metal concentration than the hydroxide, the increased solids content of the reaction mixture makes stirring more difficult and the reaction rate is considerably lower.

The gelled reaction mixture is allowed to cool to room temperature and hydrocarbon solvent (e.g., heptane) is added to give the required concentration of gadolinium, typically 100 g/l. The diluted reaction mixture is stirred to completion. The resulting product is a clear solution of low viscosity (<20 cP). Attempts to add the hydrocarbon solvent at elevated temperatures or prolonged heating of the solution to remove water (e.g., Dean-Stark distillation) can result in solutions of high viscosity, typically in excess of 200 cP. These high viscosities are not suitable for wellbore tracers because of difficulties with rapid injection into the flowing oil and subsequent mixing.

In use, some formulations of Gd tracer solutions according to the invention can react with carbonate and bicarbonate ions in formation brines and precipitate gadolinium carbonate at the tracer-solution interface. This is undesirable since it can interfere with ejection of the tracer from a tool and prevent good mixing of the tracer with the oil phase. The addition of a second carboxylic acid to the solution, such as octanoic acid or 3,5,5-trimethylhexanoic acid, can inhibit the carbonate formation.

I claim:

1. A tracer solution comprising:
   a) a gadolinium salt of a carboxylic acid of general formula

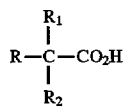

where R is an alkyl of not less than four carbon atoms, and $R_1$ and $R_2$ are selected from the group consisting of hydrogen and an alkyl group;
   b) a free branched-chain carboxylic acid;
   c) a non-polar solvent and
   d) a viscosity stabilizer selected from the group consisting of tributyl citrate, oleyl alcohol, n-cyclohexyl-p-toluenesulfonamide and di(ethylene glycol) butyl ether.

2. A tracer solution as claimed in claim 1, wherein the concentration of gadolinium in the solution is greater than about 50 g/l.

3. A tracer solution as claimed in claim 1, wherein the solution has a viscosity of less than about 20 cP.

4. A tracer solution as claimed in claim 1, wherein R is selected from the group consisting of C4 and C5 alkyl.

5. A tracer solution as claimed in claim 1, wherein $R_1$ and $R_2$ are selected from the group consisting of hydrogen, methyl and ethyl such that when $R_1$ is hydrogen, $R_2$ is methyl or ethyl.

6. A tracer solution as claimed in claim 5, wherein the free branched-chain carboxylic acid comprises an excess of the acid of formula

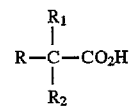

wherein R is as previously defined $R_1$ and $R_2$ are selected from the group consisting of hydrogen, methyl and ethyl, such that when $R_1$ is hydrogen, $R_2$ is methyl or ethyl.

7. A tracer solution as claimed in claim 1, wherein $R_1$ and, $R_2$ are hydrogen and the free branched-chain carboxylic acid is selected from the group consisting of 3,5,5-trimethylhexanoic acid and 2-ethylhexanoic acid.

8. A tracer solution as claimed in claim 1, wherein the non-polar solvent comprises a hydrocarbon and the solution has a density less than that of water.

9. A tracer solution as claimed in claim 1, where the gadolinium salt is present in an amount of about 30 weight % and the free branched-chain acid is present in an amount of about 20–50 mole %.

10. A tracer solution comprising:
    a) a gadolinium salt of a carboxylic acid selected from the group consisting of hexanoic acid, 2-ethylhexanoic acid, neodecanoic acid, 2-methylhexanoic acid and 2,2-dimethylhexanoic acid;
    b) a free branched-chain carboxylic acid selected from the group consisting of 2-ethylhexanoic acid, neodecanoic acid, 2-methylhexanoic acid, 2,2-dimethylhexanoic acid and 3,5,5-trimethyl hexanoic acid;
    c) a hydrocarbon solvent selected from hexane and heptane and
    d) a viscosity stabilizer selected from the group consisting of tributyl citrate, oleyl alcohol, n-cyclohexyl-p-toluensulfonamide and di(ethylene glycol) butyl ether.

11. A tracer solution as claimed in claim 10, wherein the carboxylic acid forming the gadolinium salt is selected from the group consisting of 2-ethylhexanoic acid, neodecanoic acid, 2-methylhexanoic acid and 2,2-dimethylhexanoic acid, and the free branched-chain carboxylic acid comprises an excess of the selected acid.

12. A tracer solution as claimed in claim 10, wherein the carboxylic acid forming the gadolinium salt is hexanoic acid, and the free branched-chain carboxylic acid is selected from the group consisting of 2-ethylhexanoic acid and 3,5,5-trimethyl hexanoic acid.

13. A tracer solution as claimed in claim 10, further comprising octanoic acid as a carbonate inhibitor.

14. A tracer solution as claimed in claim 10, wherein the gadolinium salt comprises gadolinium 2-ethylhexanoate, the solvent comprises heptane and the tributyl citrate is present as a viscosity stabilizer in an amount of about 3%.

* * * * *